(12) United States Patent
Koradin et al.

(10) Patent No.: US 11,021,452 B2
(45) Date of Patent: *Jun. 1, 2021

(54) PREPARATION OF SUBSTITUTED 3-ARYL-5-TRIFLUOROMETHYL-1,2,4-OXADIAZOLES

(71) Applicant: BASF SE, Ludwigshafen am Rhein (DE)

(72) Inventors: Christopher Koradin, Ludwigshafen (DE); Wassilios Grammenos, Ludwigshafen (DE); Michael Rack, Ludwigshafen (DE); Kailaskumar Borate, Navi Mumbai (IN); Roland Goetz, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/634,202

(22) PCT Filed: Jul. 21, 2018

(86) PCT No.: PCT/EP2018/069482
§ 371 (c)(1),
(2) Date: Jan. 27, 2020

(87) PCT Pub. No.: WO2019/020451
PCT Pub. Date: Jan. 31, 2019

(65) Prior Publication Data
US 2020/0157064 A1    May 21, 2020

(30) Foreign Application Priority Data
Jul. 28, 2017 (EP) ..................... 17183655

(51) Int. Cl.
*C07D 271/06* (2006.01)
(52) U.S. Cl.
CPC .................. *C07D 271/06* (2013.01)
(58) Field of Classification Search
CPC .................................. C07D 271/06
See application file for complete search history.

(56) References Cited

U.S. PATENT DOCUMENTS

2010/0280083 A1* 11/2010 Ishikawa ............... A61P 25/24
514/364

FOREIGN PATENT DOCUMENTS

| WO | WO-2015/185485 A1 | 12/2015 |
| WO | WO-2017/198852 A1 | 11/2017 |
| WO | WO-2017/207757 A1 | 12/2017 |
| WO | WO-2017/211649 A1 | 12/2017 |
| WO | WO-2017/220485 A1 | 12/2017 |
| WO | WO-2018/065414 A1 | 4/2018 |

OTHER PUBLICATIONS

Andersen, et al., "Oxadiazoles as bioisosteric transformations of carboxylic functionalities. Part I", European Journal of Medicinal Chemistry, vol. 29, Issue 5, 1994, pp. 393-399.
Brown, et al., "Reactions of Perfluoroalkyl Nitriles. VII. Perfluoroacyl Amidoximes and 3,5-Bis(perfluoroalkyl)-1,2,4-oxadiazoles", The Journal of Organic Chemistry, vol. 30, Issue 11, 1965, pp. 3734-3738.
Chu, et al., "Bioisosteric replacement of the pyrazole 3-carboxamide moiety of rimonabant. A novel series of oxadiazoles as CB1 cannabinoid receptor antagonists", Organic & Biomolecular Chemistry, vol. 6, Issue 18, Jan. 2008, pp. 3399-3407.
International Search Report and Written Opinion for PCT Patent Application No. PCT/EP2018/069482, dated Sep. 19, 2018, 4 pages.
Liu, et al., "Discovery of Potent, Selective, Orally Bioavailable Stearoyl-CoA Desaturase 1 Inhibitors", Journal of Medicinal Chemistry, vol. 50, Issue 13, Jun. 2007, pp. 3086-3100.

* cited by examiner

*Primary Examiner* — Shawquia Jackson
(74) *Attorney, Agent, or Firm* — Marshall, Gerstein & Borun LLP

(57) ABSTRACT

The present invention relates to a process for the preparation of substituted 3-aryl-5-trifluoromethyl-1,2,4-oxadiazoles (compounds I), which can be obtained through reaction of hydroxyamidine compounds of formula II with trifluoroacetyl halides IIa.

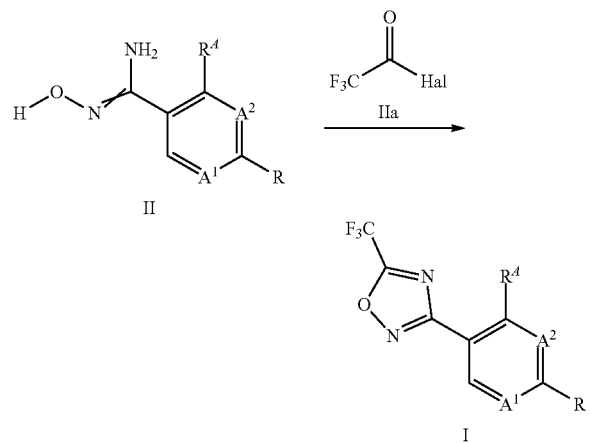

20 Claims, No Drawings

PREPARATION OF SUBSTITUTED 3-ARYL-5-TRIFLUOROMETHYL-1,2,4-OXADIAZOLES

This application is a National Stage application of International Application No. PCT/EP2018/069482 filed Jul. 21, 2018. This application also claims priority under 35 U.S.C. § 119 to EP Patent Application No. 17183655.4, filed Jul. 28, 2017.

The present invention relates to a process for the preparation of substituted 3-aryl-5-trifluoromethyl-1,2,4-oxadiazoles (compounds I), which can be obtained through reaction of hydroxyamidine compounds of formula II with trifluoroacetyl halides of formula IIa.

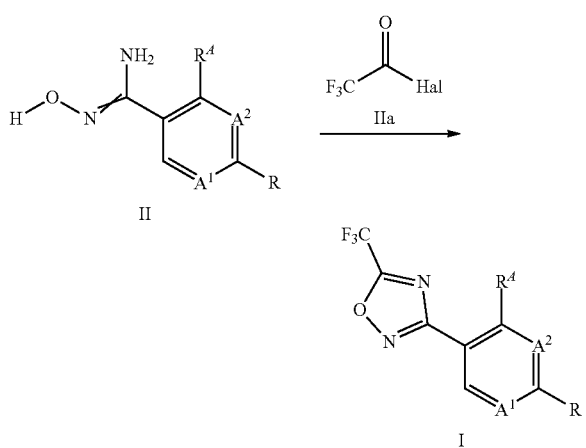

Substituted 3-aryl-5-trifluoromethyl-1,2,4-oxadiazoles are known to be useful for controlling phytopathogenic fungi, for example from WO 2015/185485 A1 and WO 2017/211649 A1. Typically, their preparation involves the formation of the oxadiazole ring through the reaction of hydroxyamidine compounds, for example compounds of formula II, with an activated derivative of trifluoroacetic acid. In the first reaction step the hydroxy group in compounds of formula II is acylated. Subsequently, the intermediate O-trifluoroacetyl amidoximes undergo ring closure with concomitant elimination of water to form the oxadiazole moiety. Trifluoroacetic acid anhydride (TFAA) is commonly used as an acylating agent. TFAA is a liquid and not very volatile. It can be handled conveniently on a laboratory scale. In the above reaction at least two equivalents of acylating agent are necessary to ascertain the complete conversion of compounds II. Hence, if TFAA is used, a total amount of at least three equivalents trifluoroacetic acid (TFA) is formed per equivalent of compounds II, which must be discarded. TFAA is rather expensive and for the sake of atom efficiency, there is an interest to reduce the excess amounts of TFA furnished during or after the ring closing reaction. Unlike the use of TFAA, the use of trifluoroacetic halides results in the formation of a much smaller amount of TFA, which makes such process more production plant friendly and simplifies the workup procedure. As a result, the production costs are significantly lower.

The preparation of fungicidally active 3-aryl-5-trifluoromethyl-1,2,4-oxadiazoles was described in WO 2017/198852, WO 2017/207757, WO 2017220485 and in WO 2018/065414. The authors suggest that the oxadiazoles may be prepared from amidoximes by treatment with trifluoroacetyl chloride (TFACl) or trifluoroacetyl fluoride (TFAF) in the presence of a solvent, optionally in the presence of a base. However, all synthetic examples were prepared using TFAA.

Brown et al. (*Journal of Organic Chemistry* 1965, 30, 3734-3738) describe the preparation of perfluoroalkyl amidoximes and their use for the preparation of 3,5-bis(perfluoroalkyl)-1,2,4-oxadiazoles in two consecutive steps. In the first step the perfluoroalkyl amidoximes are reacted with one equivalent perfluoroacyl chloride to give O-perfluoroacyl perfluoroalkyl amidoximes. In the second step, these intermediates undergo a cyclisation/dehydration step in the presence of phosphorus pentoxide at temperatures between 200-300° C. Brown et al. also suggest conducting step 1 and step 2 in the presence of an excess of perfluoroacyl chloride, which does not require the presence of a separate dehydrating agent. The reaction sequence is conducted in substance, i.e. in the absence of a further solvent. One example describes the synthesis of 3,5-bis(perfluoropropyl)-1,2,4-oxadiazole, which employs perfluorobutyryl chloride and does not employ a solvent. It is taught, that this type of reaction needs to be carried out at temperatures of 200° C. in a sealed ampoule. Brown et al. mention that the formation of 3,5-bis(trifluoromethyl)-1,2,4-oxadiazole and the use of TFACl was conducted following a (general) procedure, which uses tetrahydrofuran as a solvent.

It was now found that 3-aryl-5-trifluoromethyl-1,2,4-oxadiazoles can be obtained by reacting arylamidoximes of formula II with trifluoroacetyl halides of formula IIa, in particular TFACl or TFAF, whereas the process is characterized in that the compounds of formula II and IIa are used in substance. The term "in substance" in the context of the present invention shall mean that the process is conducted by contacting compounds II and IIa in the absence of any further solvent.

TFACl and TFAF (boiling points: TFACl: −27° C., TFAF: −59° C. at atmospheric pressure) are gases at temperatures, which are amenable for reactions on an industrial scale. Amidoximes of formula II are solids at room temperature. They typically melt at temperatures above 100° C. and begin to decompose at temperatures of more than 100° C., oftentimes upon melting. Since they are strong nucleophiles, the reaction with highly reactive TFACl or TFAF is highly exothermic. In general, a skilled person prefers to carry out chemical transformations under homogeneous reaction conditions using an inert solvent because a solution of the reactions components provides optimal mass transport, heat transport and the solvent molecules may further influence the kinetics of a reaction or the reactivity of the reactive components to the advantage of the desired chemical process. These effects are appreciated to alleviate the potential negative consequences of highly exothermic reactions. In particular, inhomogeneous reactions do not allow for a sufficient control of the process. In highly exothermic reactions, local overheating at the phase interface between, for example, the solid and the gaseous reaction components are likely to occur in the presence of thermolabile reaction components such as arylamidoximes of formula II. In the absence of a solvent, the person skilled in the art would expect the formation of more side-products, decomposition of the amidoximes II or even the risk of an explosive combustion, especially on a large industrial scale. This defers the skilled person of using such reaction conditions.

The process described by Brown et al. uses temperatures of 200° C. in a sealed vessel, i.e. presumably under pressure, which was found to be suitable to react perfluoroalkyl amidoximes.

In view of the objective of the present invention, the skilled person would not have referred to the teaching of Brown et al. because the high reaction temperatures are not compatible with the thermal behavior of arylamidoximes of formula II, even more since the reaction with halides of formula IIa is exothermic. As said before, the inventors of the present invention have found that high temperatures lead to considerable decomposition of the amidoximes of formula II and formation of unwanted side-products, which results in substantial yield losses.

In view of the above, it was an object of the present invention to overcome the disadvantages of the known processes and to provide an improved and more economical and production plant friendly process, which enables the preparation of large amounts of 3-aryl-5-trifluoromethyl-1,2,4-oxadiazoles on an industrial scale in high yield and with low amounts of side-products. The inventors have surprisingly found, that the process of the present invention provides a solution for these problems. The process of the present invention is eco-friendly and cost efficient as it does not require the use of a solvent. A separation of the reaction product and the solvent is not necessary after the reaction is completed. The reaction product obtained from the reaction between compounds II and IIa is typically a liquid, which is advantageous for a technical set-up with continuous reaction processes. The reaction product may be employed in subsequent transformations without the need to change the reaction vessel (one-pot-reaction).

Accordingly the present invention relates to a process for preparing compounds of formula I,

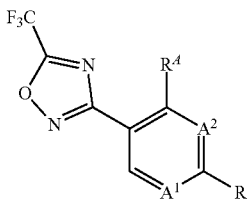

I wherein
$A^1$ is N or CH;
$A^2$ is N or CH;
$R^A$ is hydrogen or halogen;
R is methyl, trichloromethyl, ethyl, iso-propyl, OH, SH, cyano, halogen, $CH_2F$, $CHF_2$, 2,2,2-trifluoroethyl, cyclopropyl, —COOH, —COOR$^1$, —C(=W)NR$^1$R$^2$, —CR$^3$R$^4$NR$^1$R$^2$, —CR$^3$R$^4$OR$^1$, —CR$^3$(=NR$^1$), —CR$^3$(=O), —CR$^3$R$^4$COOH, —CR$^3$R$^4$COR$^1$, —CR$^3$R$^4$C(=W)NR$^1$R$^2$, —OCR$^3$R$^4$COOH, —OCR$^3$R$^4$COR$^1$, —OCR$^3$R$^4$C(=W)NR$^1$R$^2$, —CR$^3$R$^4$NR$^2$C(=W)R$^1$, —CR$^3$R$^4$S(=O)$_2$R$^1$, or —CR$^3$R$^4$NR$^2$S(=O)$_2$R$^1$;
W is O or S;
$R^2$ is hydrogen, formyl, $C_1$-$C_6$-alkyl, $C_2$-$C_6$-alkenyl, $C_2$-$C_6$-alkynyl, $C_1$-$C_6$-alkoxy, $C_3$-$C_{11}$-cycloalkyl, $C_3$-$C_8$-cycloalkenyl, $C_3$-$C_{11}$-cycloalkyl-$C_1$-$C_4$-alkyl, phenyl-$C_1$-$C_4$-alkyl, phenyl, pyridinyl, —C(=O)—($C_1$-$C_6$-alkyl), —C(=O)—($C_3$-$C_{11}$-cycloalkyl), —C(=O)—($C_1$-$C_6$-alkoxy) and —N(R$^2$12;
$R^{2a}$ is independently selected from the group consisting of hydrogen, OH, $C_1$-$C_6$-alkyl, $C_2$-$C_6$-alkenyl, $C_2$-$C_6$-alkynyl, $C_3$-$C_{11}$-cycloalkyl, $C_3$-$C_8$-cycloalkenyl, $C_1$-$C_6$-alkoxy, $C_1$-$C_4$-alkoxy-$C_1$-$C_4$-alkyl and $C_1$-$C_6$-alkylthio;
and wherein any of the aliphatic or cyclic groups in $R^2$ are unsubstituted or substituted with 1, 2, 3 or up to the maximum possible number of identical or different radicals selected from the group consisting of halogen, hydroxy, oxo, cyano, $C_1$-$C_6$-alkoxy and $C_3$-$C_{11}$-cycloalkyl;
$R^1$ is $C_1$-$C_6$-alkyl, $C_1$-$C_6$-alkoxy, $C_3$-$C_{11}$-cycloalkyl, $C_3$-$C_8$-cycloalkenyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkylamino, —C(=O)—($C_1$-$C_6$-alkyl), —C(=O)—($C_1$-$C_6$-alkoxy), phenyl-$C_1$-$C_4$-alkyl, phenyl-$C_1$-$C_4$-alkenyl, phenyl-$C_1$-$C_4$-alkynyl, heteroaryl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein the heteroaryl group in the group heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms with the provision that the heterocycle cannot contain 2 contiguous atoms selected from O and S; and wherein any of the above-mentioned aliphatic or cyclic groups are unsubstituted or substituted with 1, 2, 3 or up to the maximum possible number of identical or different groups $R^{1a}$; or
$R^1$ and $R^2$, together with the nitrogen atom to which $R^2$ is attached, and together with interjacent group —C(=W)—, if present, which is located between said nitrogen atom and the group $R^1$, form a saturated or partially unsaturated mono- or bicyclic 3- to 10-membered heterocycle, wherein the heterocycle includes beside one nitrogen atom and one or more carbon atoms no further heteroatoms or 1, 2 or 3 further heteroatoms independently selected from N, O and S as ring member atoms with the provision that the heterocycle cannot contain 2 contiguous atoms selected from O and S; and wherein the heterocycle is unsubstituted or substituted with 1, 2, 3, 4 or up to the maximum possible number of identical or different groups $R^{1a}$; or
if $R^2$ is —N(R$^{2a}$)$_2$, $R^1$ and one of the two groups $R^{2a}$, together with the nitrogen atom to which $R^{2a}$ is attached, and together with interjacent groups, which are located between said nitrogen atom and the group $R^1$, form a saturated or partially unsaturated mono- or bicyclic 3- to 10-membered heterocycle, wherein the heterocycle includes beside two nitrogen atoms and one or more carbon atoms no further heteroatoms or 1, 2 or 3 further heteroatoms independently selected from N, O and S as ring member atoms with the provision that the heterocycle cannot contain 2 contiguous atoms selected from O and S; and wherein the heterocycle is unsubstituted or substituted with 1, 2, 3, 4 or up to the maximum possible number of identical or different groups $R^{1a}$;
$R^{1a}$ is halogen, oxo, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, —NHSO$_2$—$C_1$-$C_4$-alkyl, (C=O)—$C_1$-$C_4$-alkyl, C(=O)—$C_1$-$C_4$-alkoxy, $C_1$-$C_6$-alkylsulfonyl, hydroxy$C_1$-$C_4$-alkyl, C(=O)—$NH_2$, C(=O)—NH($C_1$-$C_4$-alkyl), $C_1$-$C_4$-alkylthio-$C_1$-$C_4$-alkyl, $C_1$-$C_4$-alkylamino-$C_1$-$C_4$-alkyl, aminocarbonyl-$C_1$-$C_4$-alkyl or $C_1$-$C_4$-alkoxy-$C_1$-$C_4$-alkyl;

R³, R⁴ independently of each other are selected from the group consisting of hydrogen, halogen, cyano, $C_1$-$C_4$-alkenyl, $C_1$-$C_4$-alkynyl, $C_1$-$C_4$-haloalkyl and $C_1$-$C_4$-alkoxy; or R³ and R⁴ together with the carbon atom to which they are bound form a cyclopropyl group;

the process comprising reacting a compound of formula II,

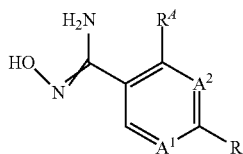

wherein the variables $A^1$, $A^2$, R and $R^4$ are as defined above for compounds of formula I, with a trifluoroacetyl halide of formula IIa,

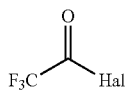

wherein Hal is chlorine or fluorine; and whereas the process is characterized in that the compounds of formula II and IIa are used in substance.

In a preferred embodiment the group Hal in compounds of formula IIa is chlorine.

The reaction is typically carried out at atmospheric pressure or at elevated pressure. The term "elevated pressure" in the context of the present invention means a pressure above 100 kPa. Typically, the reaction vessel or reactor is evacuated before or after introducing the amidoxime II and is then flushed with an inert gas, for example with nitrogen or argon. If the reaction is carried out at elevated pressure, the amidoxime II is added to a pressure reactor and the pressure reactor is sealed after the inert gas has been introduced into the reaction vessel. After setting the initial reaction temperature of the reactor and its contents, the halide IIa is introduced into the reactor, under agitation or without agitation. Since the reaction mixture is a liquid, agitation is not a prerequisite to achieve the complete conversion of the reactants and it is sufficient to bring the halide IIa into contact with the amidoxime II. It is advantageous to configure the reactor vessel so that the gaseous halide IIa can continuously stream through a bed of the solid amidoxime II or through the liquid reaction mixture. In one preferred aspect, the gaseous halide IIa might also be passed through the reaction medium in a closed circuit within the reaction vessel. In another preferred embodiment the reaction is carried out in an open apparatus and in the presence of a condenser, which is sufficiently cold to condense the halide IIa but not cold enough to liquify the hydrogen chloride that is furnished during the reaction in case that halide IIa is TFACl. In this way TFACl is kept inside the reaction vessel, whereas hydrogen chloride may be removed continuously.

In one embodiment the reaction is conducted using 1 to 10 molar equivalents of the halide IIa, based on the amount of the amidoxime II. Preferably, 2 to 5 molar equivalents are used, particularly 2 to 3 molar equivalents are used, based on the amount of the amidoxime II.

The reaction temperature of the above process is preferably in the range of −40° C. to 100° C.; preferably in the range of 0° C. to 100° C.; more preferably in the range of 20° C. to 80° C.; particularly in the range of 40° C. to 75° C.

The reaction is carried out within 10 minutes to 24 hours, preferably within 30 minutes to 8 hours, more preferably within 30 minutes to 120 minutes, particularly within 30 minutes and 90 minutes.

The present inventors have found that the above reaction may be slow at low temperatures, for example at 25° C. On the other hand, temperatures above 50° C. at the outset of the reaction might lead to the formation of unwanted side products, especially at elevated pressure and/or in the presence of a large excess of halide IIa. Especially at the beginning of the reaction it is advantageous to work with lower temperatures.

In one embodiment of the invention the temperature of the reaction mixture, which is obtained after the introduction of the halide IIa into the reaction vessel, is raised starting from an initial reaction temperature T1 to a reaction temperature T2, which is higher than T1. This procedure allows for a complete conversion of the reactants within shorter reaction times and minimizes the amount of unwanted side products. The temperature may be raised steadily over the whole time period that is needed for complete conversion. The temperature may also be raised stepwise, in two steps from T1 to T2, or in several steps to reach the final temperature T2. It is preferred to start the reaction at a temperature T1 between 0° C. to 50° C. and to raise the temperature of the reaction mixture, steadily or in one or more steps, to a higher temperature T2, which is within the range between T1 and a maximum of 100° C.

In another preferred embodiment the reaction is started at a temperature T1 between 20° C. to 50° C. and then the reaction mixture is heated, steadily or in one or more steps, to a higher temperature T2, which is within the range between T1 and a maximum of 80° C.

In one preferred embodiment the reaction is started at a temperature T1 between 40° C. to 50° C. and then the reaction mixture is heated, steadily or in one or more steps, to a higher temperature T2, which is within the range between T1 and a maximum of 75° C.

In a preferred embodiment, the reaction is carried out under elevated pressure to reduce the reaction time. The pressure is preferably chosen between 100 and 1000 kPa; more preferably between 100 and 600 kPa; particularly between 200 and 500 kPa. In one embodiment the reaction is carried out at elevated pressure, whereas the pressure is released once or more often until completion of the reaction is achieved. This procedure removes larger parts of the hydrogen chloride or hydrogen fluoride from the reactor. After each release, the reactor is recharged with halide IIa.

The present inventors have found that the yield and purity of the compound of formula I can be further improved under specific reaction conditions. Under elevated pressure and in the presence of a high excess of halide IIa, especially in combination with elevated temperatures, for example temperatures of 50° C. and more, decomposition of the amidoxime II and the formation of unwanted side products is observed. Especially at the beginning of the reaction it is advantageous to work with lower pressures, optionally in combination with lower temperatures. Both, pressure and temperature, may be raised later and without negative impact on yield and purity of the product.

The detrimental effects associated with elevated pressures can be mitigated by keeping the amount if the halide IIa low at the beginning of the reaction. The addition of an inert gas to the halide IIa may therefore cause the reaction to proceed more selectively. For reactions under pressure, the inert gas may contribute to establishing a desired internal pressure. Accordingly, it is advantageous to conduct the process at elevated pressure and in the presence of 2 to 5 equivalents, preferably 2 to 3 equivalents of the halide IIa, based on the amount of the amidoxime II; and wherein the gaseous halide IIa is mixed with an inert gas, for example with nitrogen or argon. It is preferred to choose the ratio of halide IIa to the inert gas in the range of 5:1 to 1:5, more preferably in the range of 3:1 to 1:3, particularly in the range of 1:1 to 5:1, more particularly in the range of 1:1 to 3:1, based on the partial pressures of the gaseous mixture components.

In a preferred embodiment the reaction is carried out at a pressure between 100 and 600 kPa, at a temperature in the range between 0° C. to 100° C., whereas the reaction starts at a temperature T1 between 0° C. to 50° C. and the temperature of the reaction mixture is then raised, steadily or in one or more steps, to a higher temperature T2, which is within the range between T1 and a maximum of 100° C.; the procedure is carried out in the presence of 2 to 5 equivalents of the halide IIa, based on the amount of the amidoxime II; the gaseous halide IIa is mixed with an inert gas, for example with nitrogen or argon, with a ratio of halide IIa to the inert gas in the range of 5:1 to 1:5, based on the partial pressures of the gaseous mixture components.

In another preferred embodiment the reaction is carried out at a pressure between 100 and 600 kPa, at a temperature in the range between 20° C. to 80° C., whereas the reaction starts at a temperature T1 between 20° C. to 50° C. and the temperature of the reaction mixture is then raised, steadily or in one or more steps, to a higher temperature T2, which is within the range between T1 and a maximum of 80° C.; the procedure is carried out in the presence of 2 to 5 equivalents of the halide IIa, based on the amount of the amidoxime II; the gaseous halide IIa is mixed with an inert gas, for example with nitrogen or argon, with a ratio of halide IIa to the inert gas in the range of 5:1 to 1:5, based on the partial pressures of the gaseous mixture components.

In another preferred embodiment the reaction is carried out at a pressure between 200 and 500 kPa, at a temperature in the range between 20° C. to 80° C., whereas the reaction starts at a temperature T1 between 20° C. to 50° C. and the temperature of the reaction mixture is then raised, steadily or in one or more steps, to a higher temperature T2, which is within the range between T1 and a maximum of 80° C.; the procedure is carried out in the presence of 2 to 3 equivalents of the halide IIa, based on the amount of the amidoxime II; the gaseous halide IIa is mixed with an inert gas, for example with nitrogen or argon, with a ratio of halide IIa to the inert gas in the range of 3:1 to 1:3, based on the partial pressures of the gaseous mixture components.

In still another preferred embodiment the reaction is carried out at a pressure between 200 and 500 kPa, at a temperature in the range between 40° C. to 75° C., whereas the reaction starts at a temperature T1 between 40° C. to 50° C. and the temperature of the reaction mixture is then raised, steadily or in one or more steps, to a higher temperature T2, which is within the range between T1 and a maximum of 75° C.; the procedure is carried out in the presence of 2 to 3 equivalents of the halide IIa, based on the amount of the amidoxime II; the gaseous halide IIa is mixed with an inert gas, for example with nitrogen or argon, with a ratio of halide IIa to the inert gas in the range of 3:1 to 1:3, based on the partial pressures of the gaseous mixture components.

The amidoxime compounds of formula II can be obtained from cyano compounds V,

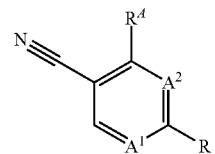

by treatment with hydroxylamine or a salt thereof, for example the hydrochloride salt, in the presence of a base, preferably triethylamine, sodium hydroxide or sodium methylate, in a suitable solvent, such as methanol, ethanol or water, or a mixture of these solvents, at a temperature between 0° C. and 100° C. For related examples see Kitamura, S. et al *Chem. Pharm. Bull.* 2001, 49, 268 or any one of the patent references cited above. Compounds of formula V are either commercially available or may be prepared using standard procedures known to a person skilled in the art from readily available starting materials.

In a further embodiment, a compound of formula I, in which R is methyl, is converted into valuable chemical products or intermediates. Accordingly, compounds of formula I, wherein R is methyl, can be further chlorinated to obtain a compound of formula Ib

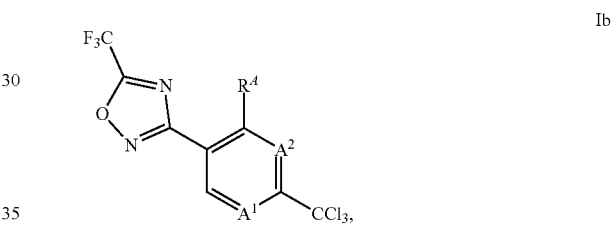

wherein the variables $A^1$, $A^2$ and $R^A$ in compounds I and Ib are as defined or preferably defined herein.

The chlorination of the methyl group R of compounds of formula I can be achieved using suitable chlorinating agents, for example molecular chlorine, N-chlorosuccinimide, trichloroisocyanuric acid, sulfuryl chloride or phosphorus pentachloride. The chlorination is conducted at temperatures between 0° C. and 200° C., preferably between 60° C. and 150° C., under irradiation or in the presence of radical starters, for example azobis(isobutyronitrile) or dibenzoyl peroxide. For reference, see *J. Am. Chem. Soc.* 1951, 73, 455.

In one embodiment, the chlorination is carried out in the presence of at least one inert organic solvent, or mixtures of such solvents. The term "inert organic solvent" means an organic solvent, which does not enter into any appreciable reaction with either the reactants or the products under the reaction conditions of the process of this invention. The inert organic solvent used in the process is preferably selected from halogenated aliphatic hydrocarbons and halogenated aromatic hydrocarbons, such as dichloromethane, tetrachloromethane, dichloroethane, chlorobenzene, homologues of dichlorobenzenes or 1,2,4-trichlorobenzene. In a particularly preferred embodiment the chlorination step is conducted in substance, for example with the liquid reaction product, which is directly obtained after the reaction of compounds II and IIa and in the absence of a further solvent, as described above.

The chlorination can be performed in the presence or absence of TFA impurities originating from the previous reaction. TFA can be removed during the chlorination process via distillation or separately by distillation before carrying out the chlorination step. After completion of the reaction the reaction mixture is worked up in the usual manner or it can be used directly in the next step.

In a further preferred embodiment, the compound of formula Ib is hydrolyzed to obtain a compound of formula III

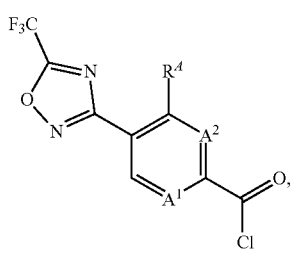

III wherein the variables $A^1$, $A^2$ and $R^A$ in compounds Ib and III are as defined or preferably defined herein.

In one embodiment this transformation is carried out in the presence of catalytic amounts of a lewis acid and water to obtain a compound of formula III, as described in WO 2007/063028 A2 on pages 42-43. Preferably, the lewis acid is a metal salt, for example aluminum(III) chloride or iron(III) chloride, particularly iron(III) chloride. The lewis acid is used in sub-stoichiometric or catalytic amounts, for example 0.001 to 0.5 molar equivalents, preferably 0.002 to 0.2 molar equivalents, more preferably 0.005 to 0.1 molar equivalents, based on the amount of the compound of formula Ib.

In one embodiment, the hydrolysis step is carried out in the presence of at least one inert organic solvent, or mixtures of such solvents. The inert organic solvent used in the process of this invention is preferably selected from non-halogenated aliphatic hydrocarbons, non-halogenated cycloaliphatic hydrocarbons, halogenated aliphatic hydrocarbons, halogenated aromatic hydrocarbons, amides, ethers, esters, ketones, nitriles.

In a preferred embodiment, the hydrolysis step is carried out in the absence of a solvent, i.e. in substance. Under these conditions the trichloromethyl compound Ib or the crude material comprising Ib, which was obtained from the previous reaction step, is heated to a temperature, where such material is a molten mass.

The amount of water in the hydrolysis step is between 0.8 to 1.5 molar equivalents, preferably between 0.95 to 1.05 molar equivalents, based on the amount of the compound Ib. The reaction is carried out at temperatures between 20° C. and 200° C., preferably between 80° C. and 130° C. After completion of the reaction the reaction mixture is worked up in the usual manner or it can be used directly in the next step.

In an especially preferred embodiment, the compound of formula III is reacted with an amine of formula IV to obtain a compound of formula Ic,

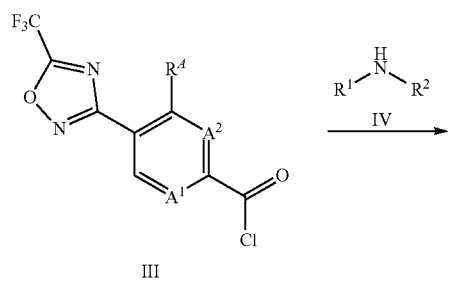

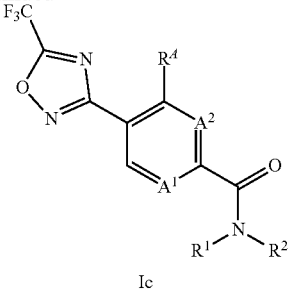

Ic wherein the variables $A^1$, $A^2$, $R^A$, $R^1$ and $R^2$ in compounds of formulae III and IV are as defined or preferably defined herein.

A skilled person will recognize that oxadiazole compounds of type Ic can be accessed by treating benzoic acid chloride of formula III with an amine of formula IV. The reaction is preferably carried out in a suitable inert organic solvent, such as non-halogenated aliphatic hydrocarbons, non-halogenated cycloaliphatic hydrocarbons, halogenated aliphatic hydrocarbons, halogenated aromatic hydrocarbons, amides, ethers, esters, ketones, nitriles; for example, N,N-dimethylformamide, dichloromethane or tetrahydrofuran; preferably at a temperature between −20° C. and 200° C., preferably between 0° C. and 80° C., and optionally in the presence of a base such as pyridine, triethylamine or N,N-diisopropylethylamine, or under conditions described in the literature for an amide coupling. For examples, see Valeur, E.; Bradley, M. *Chem. Soc. Rev.* 2009, 38, 606 and Chinchilla, R., Najera, C. *Chem. Soc. Rev.* 2011, 40, 5084. After completion of the reaction the reaction mixture is worked up in the usual manner.

In another especially preferred embodiment, the compound of formula Ic is used to obtain a compound of formula Id

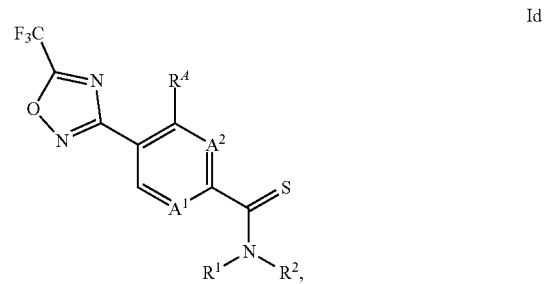

wherein the variables $A^1$, $A^2$, $R^A$, $R^1$ and $R^2$ in compounds of formulae Ic and Id are as defined or preferably defined herein.

Compounds of formula Ib can be prepared from compounds of formula Ic through treatment with Lawesson's reagent or phosphorus pentasulfide in an inert organic solvent, such as non-halogenated aliphatic hydrocarbons, non-halogenated cycloaliphatic hydrocarbons, halogenated aliphatic hydrocarbons, halogenated aromatic hydrocarbons, amides, ethers, esters, ketones, nitriles; for example toluene, tetrahydrofuran, dioxane or ethyl acetate; at a temperature between 0° C. and 130° C., preferentially between 60° C. and 80° C. For examples, see *Eur. J. Med. Chem.* 2011, 46(9), 3917-3925; *Synthesis* 2003, 13, 1929-1958; WO 2006/0123242; WO 2010/086820; WO 2014/0151863. After completion of the reaction the reaction mixture is worked up in the usual manner.

Further embodiments relate to the meaning of the variables $R^1$ and $R^2$ in compounds of formulae IV, Ic and Id.

In one embodiment in compounds of formulae IV, Ic and Id $R^1$ is $C_1$-$C_6$-alkyl, $C_2$-$C_6$-alkenyl, $C_2$-$C_6$-alkynyl, $C_1$-$C_6$-alkoxyimino-$C_1$-$C_4$-alkyl, $C_3$-$C_{11}$-cycloalkyl, $C_3$-$C_8$-cycloalkenyl, phenyl-$C_1$-$C_4$-alkyl, heteroaryl-$C_1$-$C_4$-alkyl, phenyl or heteroaryl; and wherein the heteroaryl group is a 5- or 6-membered aromatic heterocycle, wherein the ring includes besides carbon atoms 1, 2, 3 or 4 heteroatoms selected from N, O and S as ring member atoms; and wherein any of the aliphatic or cyclic groups are unsubstituted or substituted with 1, 2, 3 or up to the maximum possible number of identical or different radicals selected from the group consisting of halogen, cyano, $C_1$-$C_6$-alkyl and $C_1$-$C_6$-alkoxy; and $R^2$ is hydrogen, formyl, $C_1$-$C_6$-alkyl, $C_1$-$C_6$-alkoxy, $C_2$-$C_6$-alkenyl, propargyl, $C_3$-$C_8$-cycloalkyl, $C_3$-$C_8$-cycloalkenyl, $C_3$-$C_8$-cycloalkyl-$C_1$-$C_4$-alkyl, phenyl, $C_1$-$C_6$-alkylamino or di$C_1$-$C_6$-alkylamino; and wherein any of the aliphatic or cyclic groups are unsubstituted or substituted with 1, 2, 3, 4 or up to the maximum possible number of identical or different radicals selected from the group consisting of halogen, cyano, $C_1$-$C_6$-alkyl and $C_1$-$C_6$-alkoxy.

In another embodiment in compounds of formulae IV, Ic and Id $R^1$ is methyl, ethyl, n-propyl, iso-propyl, n-butyl, sec-butyl, iso-butyl, cyclopropyl, 2-methoxyiminoethyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, methyl, ethyl, methoxy, trifluoromethyl, trifluoromethoxy, difluoromethyl, difluoromethoxy and cyclopropyl; and $R^2$ is hydrogen, methyl or ethyl.

In a further embodiment in compounds of formulae IV, Ic and Id $R^1$ is methyl, 2-methoxyiminoethyl, bicyclo[1.1.1]pentan-1-yl, 2-fluoro-phenyl, 4-fluoro-phenyl, or 2-difluoromethoxy-phenyl;

$R^2$ is hydrogen.

Further embodiments with regard to the meaning of the variables in compounds of formulae I, Ib, Ic, Id, II and III are as follows:

Embodiment E1: $A^1$ and $A^2$ are CH and $R^4$ is hydrogen.
Embodiment E2: $A^1$ and $A^2$ are CH and $R^4$ is fluorine.
Embodiment E3: $A^1$ is N, $A^2$ is CH and $R^4$ is hydrogen.
Embodiment E4: $A^1$ and $A^2$ are CH, $R^4$ is hydrogen, and R is methyl, trichloromethyl, COOH, OH, SH, cyano, chlorine or bromine.
Embodiment E5: $A^1$ and $A^2$ are CH, $R^4$ is fluorine, and R is methyl, trichloromethyl, COOH, OH, SH, cyano, chlorine or bromine.
Embodiment E6: $A^1$ is N, $A^2$ is CH, $R^4$ is hydrogen, and R is methyl, trichloromethyl, COOH, OH, SH, cyano, chlorine or bromine.
Embodiment E7: $A^1$ and $A^2$ are CH, $R^4$ is hydrogen, and R is methyl, trichloromethyl, OH or SH; particularly R is methyl.
Embodiment E8: $A^1$ and $A^2$ are CH, $R^4$ is fluorine, and R is methyl, trichloromethyl, OH or SH; particularly R is methyl.
Embodiment E9: $A^1$ is N, $A^2$ is CH, $R^4$ is hydrogen, and R is methyl, trichloromethyl, OH or SH; particularly R is methyl.
Embodiment E10: the combination of variables $A^1$, $A^2$, $R^4$ corresponds to any one of the Embodiments E1, E2 or E3 defined above, and R is methyl.

In one embodiment the present invention relates to a process for preparing compounds of formula I, wherein the combination of variables $A^1$, $A^2$, $R^4$ corresponds to any one of the Embodiments E1, E2 or E3 defined above; and R is methyl, trichloromethyl, ethyl, iso-propyl, OH, SH, cyano, halogen, $CH_2F$, $CHF_2$, 2,2,2-trifluoroethyl, cyclopropyl, —COOH, —COOR$^1$ or —C(=W)NR$^1$R$^2$;
W is O or S;
$R^1$ $C_1$-$C_6$-alkyl, $C_2$-$C_6$-alkenyl, $C_2$-$C_6$-alkynyl, $C_1$-$C_6$-alkoxyimino-$C_1$-$C_4$-alkyl, $C_3$-$C_8$-cycloalkyl, $C_3$-$C_8$-cycloalkenyl, phenyl-$C_1$-$C_4$-alkyl, heteroaryl-$C_1$-$C_4$-alkyl, phenyl or heteroaryl; and wherein the heteroaryl group is a 5- or 6-membered aromatic heterocycle, wherein the ring includes besides carbon atoms 1, 2, 3 or 4 heteroatoms selected from N, O and S as ring member atoms; and wherein any of the aliphatic or cyclic groups are unsubstituted or substituted with 1, 2, 3 or up to the maximum possible number of identical or different radicals selected from the group consisting of halogen, cyano, $C_1$-$C_6$-alkyl and $C_1$-$C_6$-alkoxy;

$R^2$ is hydrogen, formyl, $C_1$-$C_6$-alkyl, $C_1$-$C_6$-alkoxy, $C_2$-$C_6$-alkenyl, propargyl, $C_3$-$C_8$-cycloalkyl, $C_3$-$C_8$-cycloalkenyl, $C_3$-$C_8$-cycloalkyl-$C_1$-$C_4$-alkyl, phenyl, $C_1$-$C_6$-alkylamino or di$C_1$-$C_6$-alkylamino; and wherein any of the aliphatic or cyclic groups are unsubstituted or substituted with 1, 2, 3, 4 or up to the maximum possible number of identical or different radicals selected from the group consisting of halogen, cyano, $C_1$-$C_6$-alkyl and $C_1$-$C_6$-alkoxy.

In one embodiment the present invention relates to a process for preparing compounds of formula I, wherein the combination of variables $A^1$, $A^2$, $R^4$ corresponds to any one of the Embodiments E1, E2 or E3 defined above; and R is —COOH, —COOR$^1$ or —C(=W)NR$^1$R$^2$;
W is O or S;
$R^1$ is methyl, ethyl, n-propyl, iso-propyl, n-butyl, sec-butyl, iso-butyl, 2-methoxyiminoethyl, cyclopropyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, methyl, ethyl, methoxy, trifluoromethyl, trifluoromethoxy, difluoromethyl, difluoromethoxy and cyclopropyl.

$R^2$ is hydrogen, methyl or ethyl.

In one embodiment the present invention relates to a process for preparing compounds of formula I, wherein the combination of variables $A^1$, $A^2$, $R^4$ corresponds to any one of the Embodiments E1, E2 or E3 defined above; and R is —COOH, —COOR$^1$ or —C(=W)NR$^1$R$^2$;
W is O or S;
$R^1$ is methyl, ethyl, n-propyl, iso-propyl, n-butyl, sec-butyl, iso-butyl, 2-methoxyiminoethyl, cyclopropyl, bicyclo[1.1.1]pentan-1-yl, or phenyl; and wherein the phenyl group is unsubstituted or substituted with 1 radical selected from the group consisting of fluorine and 2-difluoromethoxy-phenyl;

$R^2$ is hydrogen, methyl or ethyl.

In one embodiment the present invention relates to a process for preparing compounds of formula I, wherein the combination of variables $A^1$, $A^2$, $R^4$ corresponds to any one of the Embodiments E1, E2 or E3 defined above; and
R is —C(=O)NR$^1$R$^2$;
R$^1$ is methyl, 2-methoxyiminoethyl, bicyclo[1.1.1]pentan-1-yl, 2-fluoro-phenyl, 4-fluoro-phenyl, or 2-difluoromethoxy-phenyl;
R$^2$ is hydrogen.

In one embodiment the present invention relates to a process for preparing compounds of formula I, wherein the combination of variables $A^1$, $A^2$, $R^4$ corresponds to any one of the Embodiments E1, E2 or E3 defined above; and
R is —C(=S)NR$^1$R$^2$;
R$^1$ is methyl, 2-methoxyiminoethyl, bicyclo[1.1.1]pentan-1-yl, 2-fluoro-phenyl, 4-fluoro-phenyl, or 2-difluoromethoxy-phenyl;
R$^2$ is hydrogen.

In a further embodiment the present invention relates to a process for preparing compounds of formula I, wherein
$A^1$ and $A^2$ are CH;
$R^4$ is hydrogen;
R is —C(=O)NR$^1$R$^2$;
R$^1$ is methyl, 2-methoxyiminoethyl, bicyclo[1.1.1]pentan-1-yl, 2-fluoro-phenyl, 4-fluoro-phenyl, or 2-difluoromethoxy-phenyl;
R$^2$ is hydrogen.

In a further embodiment the present invention relates to a process for preparing compounds of formula I, wherein
$A^1$ and $A^2$ are CH;
$R^4$ is hydrogen;
R is —C(=S)NR$^1$R$^2$;
R$^1$ is methyl, 2-methoxyiminoethyl, bicyclo[1.1.1]pentan-1-yl, 2-fluoro-phenyl, 4-fluoro-phenyl, or 2-difluoromethoxy-phenyl;
R$^2$ is hydrogen.

In one embodiment the present invention relates to a process for preparing compounds of formula I, wherein the combination of variables $A^1$, $A^2$, $R^4$ corresponds to any one of the Embodiments E1, E2 or E3 defined above; and
R is —CF$_2$COOH, —CF$_2$COR$^1$ or —CF$_2$C(=O)NR$^1$R$^2$;
R$^1$ $C_1$-$C_6$-alkyl, $C_2$-$C_6$-alkenyl, $C_2$-$C_6$-alkynyl, $C_1$-$C_6$-alkoxyimino-$C_1$-$C_4$-alkyl, $C_3$-$C_8$-cycloalkyl, $C_3$-$C_8$-cycloalkenyl, phenyl-$C_1$-$C_4$-alkyl, heteroaryl-$C_1$-$C_4$-alkyl, phenyl or heteroaryl; and wherein the heteroaryl group is a 5- or 6-membered aromatic heterocycle, wherein the ring includes besides carbon atoms 1, 2, 3 or 4 heteroatoms selected from N, O and S as ring member atoms; and wherein any of the aliphatic or cyclic groups are unsubstituted or substituted with 1, 2, 3 or up to the maximum possible number of identical or different radicals selected from the group consisting of halogen, cyano, $C_1$-$C_6$-alkyl and $C_1$-$C_6$-alkoxy;
R$^2$ is hydrogen, formyl, $C_1$-$C_6$-alkyl, $C_1$-$C_6$-alkoxy, $C_2$-$C_6$-alkenyl, propargyl, $C_3$-$C_8$-cycloalkyl, $C_3$-$C_8$-cycloalkenyl, $C_3$-$C_8$-cycloalkyl-$C_1$-$C_4$-alkyl, phenyl, $C_1$-$C_6$-alkylamino or di$C_1$-$C_6$-alkylamino; and wherein any of the aliphatic or cyclic groups are unsubstituted or substituted with 1, 2, 3, 4 or up to the maximum possible number of identical or different radicals selected from the group consisting of halogen, cyano, $C_1$-$C_6$-alkyl and $C_1$-$C_6$-alkoxy.

In one embodiment the present invention relates to a process for preparing compounds of formula I, wherein the combination of variables $A^1$, $A^2$, $R^4$ corresponds to any one of the Embodiments E1, E2 or E3 defined above; and
R is —CF$_2$COOH, —CF$_2$COR$^1$ or —CF$_2$C(=O)NR$^1$R$^2$;
R$^1$ is methyl, ethyl, n-propyl, iso-propyl, n-butyl, sec-butyl, iso-butyl, cyclopropyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, methyl, ethyl, methoxy, trifluoromethyl, trifluoromethoxy, difluoromethyl, difluoromethoxy and cyclopropyl.
R$^2$ is hydrogen, methyl or ethyl.

In another embodiment the present invention relates to a process for preparing compounds of formula I, wherein
$A^1$ and $A^2$ are CH;
$R^4$ is hydrogen or fluorine;
R is —CF$_2$COOH, —CF$_2$COR$^1$ or —CF$_2$C(=O)NR$^1$R$^2$;
R$^1$ is 1-methyl-cycloprop-1-yl or cyclobutyl;
R$^2$ is hydrogen, methyl or ethyl.

In another embodiment the present invention relates to a process for preparing compounds of formula I, wherein
$A^1$ and $A^2$ are CH;
$R^4$ is hydrogen;
R is —CF$_2$COOH, —CF$_2$COR$^1$ or —CF$_2$C(=O)NR$^1$R$^2$;
R$^1$ is 1-methyl-cycloprop-1-yl or cyclobutyl;
R$^2$ is hydrogen.

In one embodiment the present invention relates to a process for preparing compounds of formula I, wherein the combination of variables $A^1$, $A^2$, $R^4$ corresponds to any one of the Embodiments E1, E2 or E3 defined above; and
R is —OCF$_2$COOH, —OCF$_2$COR$^1$ or —OCF$_2$C(=W)NR$^1$R$^2$;
R$^1$ $C_1$-$C_6$-alkyl, $C_2$-$C_6$-alkenyl, $C_2$-$C_6$-alkynyl, $C_1$-$C_6$-alkoxyimino-$C_1$-$C_4$-alkyl, $C_3$-$C_8$-cycloalkyl, $C_3$-$C_8$-cycloalkenyl, phenyl-$C_1$-$C_4$-alkyl, heteroaryl-$C_1$-$C_6$-alkyl, phenyl or heteroaryl; and wherein the heteroaryl group is a 5- or 6-membered aromatic heterocycle, wherein the ring includes besides carbon atoms 1, 2, 3 or 4 heteroatoms selected from N, O and S as ring member atoms; and wherein any of the aliphatic or cyclic groups are unsubstituted or substituted with 1, 2, 3 or up to the maximum possible number of identical or different radicals selected from the group consisting of halogen, cyano, $C_1$-$C_6$-alkyl and $C_1$-$C_6$-alkoxy;
R$^2$ is hydrogen, formyl, $C_1$-$C_6$-alkyl, $C_1$-$C_6$-alkoxy, $C_2$-$C_6$-alkenyl, propargyl, $C_3$-$C_8$-cycloalkyl, $C_3$-$C_8$-cycloalkenyl, $C_3$-$C_8$-cycloalkyl-$C_1$-$C_4$-alkyl, phenyl, $C_1$-$C_6$-alkylamino or di$C_1$-$C_6$-alkylamino; and wherein any of the aliphatic or cyclic groups are unsubstituted or substituted with 1, 2, 3, 4 or up to the maximum possible number of identical or different radicals selected from the group consisting of halogen, cyano, $C_1$-$C_6$-alkyl and $C_1$-$C_6$-alkoxy.

In one embodiment the present invention relates to a process for preparing compounds of formula I, wherein the combination of variables $A^1$, $A^2$, $R^4$ corresponds to any one of the Embodiments E1, E2 or E3 defined above; and
R is —OCF$_2$COOH, —OCF$_2$COR$^1$ or —OCF$_2$C(=W)NR$^1$R$^2$;
R$^1$ is methyl, ethyl, n-propyl, iso-propyl, n-butyl, sec-butyl, iso-butyl, cyclopropyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, methyl, ethyl, methoxy, trifluoromethyl, trifluoromethoxy, difluoromethyl, difluoromethoxy and cyclopropyl.
R$^2$ is hydrogen, methyl or ethyl.

In another embodiment the present invention relates to a process for preparing compounds of formula I, wherein
$A^1$ and $A^2$ are CH;
$R^4$ is hydrogen or fluorine;

R is —OCF$_2$COOH, —OCF$_2$COR$^1$ or —OCF$_2$C(=W)NR$^1$R$^2$;
R$^1$ is methyl or cyclopropyl;
R$^2$ is hydrogen, methyl or ethyl.

In another embodiment the present invention relates to a process for preparing compounds of formula I, wherein
A$^1$ and A$^2$ are CH;
R$^4$ is hydrogen;
R is —OCF$_2$COOH, —OCF$_2$COR$^1$ or —OCF$_2$C(=W)NR$^1$R$^2$;
R$^1$ is methyl or cyclopropyl;
R$^2$ is hydrogen.

In one embodiment the present invention relates to a process for preparing compounds of formula I, wherein the combination of variables A$^1$, A$^2$, R$^4$ corresponds to any one of the Embodiments E1, E2 or E3 defined above; and
R is —CH$_2$NR$^2$C(=W)R$^1$, —CH$_2$S(=O)$_2$R$^1$ or —CH$_2$NR$^2$S(=O)$_2$R$^1$;
W is O or S;
R$^1$ is C$_1$-C$_6$-alkyl, C$_2$-C$_6$-alkenyl, C$_2$-C$_6$-alkynyl, C$_1$-C$_6$-alkoxyimino-C$_1$-C$_4$-alkyl, C$_3$-C$_8$-cycloalkyl, C$_3$-C$_8$-cycloalkenyl, phenyl-C$_1$-C$_4$-alkyl, heteroaryl-C$_1$-C$_4$-alkyl, phenyl or heteroaryl; and wherein the heteroaryl group is a 5- or 6-membered aromatic heterocycle, wherein the ring includes besides carbon atoms 1, 2, 3 or 4 heteroatoms selected from N, O and S as ring member atoms; and wherein any of the aliphatic or cyclic groups are unsubstituted or substituted with 1, 2, 3 or up to the maximum possible number of identical or different radicals selected from the group consisting of halogen, cyano, C$_1$-C$_6$-alkyl and C$_1$-C$_6$-alkoxy;
R$^2$ is hydrogen, formyl, C$_1$-C$_6$-alkyl, C$_1$-C$_6$-alkoxy, C$_2$-C$_6$-alkenyl, propargyl, C$_3$-C$_8$-cycloalkyl, C$_3$-C$_8$-cycloalkenyl, C$_3$-C$_8$-cycloalkyl-C$_1$-C$_4$-alkyl, phenyl, C$_1$-C$_6$-alkylamino or diC$_1$-C$_6$-alkylamino; and wherein any of the aliphatic or cyclic groups are unsubstituted or substituted with 1, 2, 3, 4 or up to the maximum possible number of identical or different radicals selected from the group consisting of halogen, cyano, C$_1$-C$_6$-alkyl and C$_1$-C$_6$-alkoxy.

In one embodiment the present invention relates to a process for preparing compounds of formula I, wherein the combination of variables A$^1$, A$^2$, R$^4$ corresponds to any one of the Embodiments E1, E2 or E3 defined above; and
R is —CH$_2$NR$^2$C(=W)R$^1$, —CH$_2$S(=O)$_2$R$^1$ or —CH$_2$NR$^2$S(=O)$_2$R$^1$;
W is O or S;
R$^1$ is methyl, ethyl, n-propyl, iso-propyl, n-butyl, sec-butyl, iso-butyl, 2-methoxyiminoethyl, cyclopropyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, methyl, ethyl, methoxy, trifluoromethyl, trifluoromethoxy, difluoromethyl, difluoromethoxy and cyclopropyl.
R$^2$ is hydrogen, methyl or ethyl.

In another embodiment the present invention relates to a process for preparing compounds of formula I, wherein
A$^1$ and A$^2$ are CH;
R$^4$ is hydrogen or fluorine;
R is —CH$_2$NR$^2$C(=W)R$^1$, —CH$_2$S(=O)$_2$R$^1$ or —CH$_2$NR$^2$S(=O)$_2$R$^1$;
W is O or S;
R$^1$ is methyl, ethyl, n-propyl, iso-propyl, n-butyl, sec-butyl, iso-butyl, 2-methoxyiminoethyl, cyclopropyl, bicyclo[1.1.1]pentan-1-yl, or phenyl; and wherein the phenyl group is unsubstituted or substituted with 1 radical selected from the group consisting of fluorine and chlorine;
R$^2$ is hydrogen, methyl or ethyl.

In another embodiment the present invention relates to a process for preparing compounds of formula I, wherein
A$^1$ and A$^2$ are CH;
R$^4$ is hydrogen or fluorine;
R is —CH$_2$NR$^2$C(=O)R$^1$, —CH$_2$S(=O)$_2$R$^1$ or —CH$_2$NR$^2$S(=O)$_2$R$^1$;
R$^1$ is methyl, ethyl, n-propyl, iso-propyl, n-butyl, sec-butyl, iso-butyl, 2-methoxyiminoethyl, cyclopropyl or bicyclo[1.1.1]pentan-1-yl;
R$^2$ is hydrogen.

In another embodiment the present invention relates to a process for preparing compounds of formula I, wherein
A$^1$ and A$^2$ are CH;
R$^4$ is hydrogen or fluorine;
R is —CH$_2$NR$^2$C(=O)R$^1$ or —CH$_2$NR$^2$S(=O)$_2$R$^1$;
R$^1$ is methyl, ethyl, n-propyl, iso-propyl, n-butyl, sec-butyl, iso-butyl, 2-methoxyiminoethyl, cyclopropyl or bicyclo[1.1.1]pentan-1-yl;
R$^2$ is hydrogen.

In another embodiment the present invention relates to a process for preparing compounds of formula I, wherein
A$^1$ and A$^2$ are CH;
R$^4$ is hydrogen or fluorine;
R is —CH$_2$S(=O)$_2$R$^1$;
R$^1$ is methyl, ethyl, n-propyl, iso-propyl, n-butyl, sec-butyl, iso-butyl, 2-methoxyiminoethyl, cyclopropyl or bicyclo[1.1.1]pentan-1-yl;
R$^2$ is hydrogen.

In the definitions of the variables given above, collective terms are used which are generally representative for the substituents in question.

The term "C$_n$-C$_m$" indicates the number of carbon atoms possible in each case in the substituent or substituent moiety in question.

The term "halogen" refers to fluorine, chlorine, bromine and iodine.

The term "oxo" refers to an oxygen atom =O, which is bound to a carbon atom or sulfur atom, thus forming, for example, a ketonyl —C(=O)— or sulfinyl —S(=O)— group.

The term "formyl" refers to a group C(=O)H.

The term "C$_1$-C$_6$-alkyl" refers to a straight-chained or branched saturated hydrocarbon group having 1 to 6 carbon atoms, for example methyl, ethyl, propyl, 1-methylethyl, butyl, 1-methylpropyl, 2-methylpropyl, and 1,1-dimethylethyl.

The term "C$_2$-C$_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "C$_2$-C$_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "C$_1$-C$_6$-haloalkyl" refers to a straight-chained or branched alkyl group having 1 to 6 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl.

The term "$C_1$-$C_6$-alkoxy" refers to a straight-chain or branched alkyl group having 1 to 6 carbon atoms (as defined above) which is bonded via an oxygen, at any position in the alkyl group, for example methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy group as defined above, wherein some or all of the hydrogen atoms may be replaced by halogen atoms as mentioned above, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy.

The terms "phenyl-$C_1$-$C_4$-alkyl or heteroaryl-$C_1$-$C_4$-alkyl" refer to alkyl having 1 to 4 carbon atoms (as defined above), wherein one hydrogen atom of the alkyl radical is replaced by a phenyl or heteroaryl radical respectively.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_4$-alkylthio-$C_1$-$C_4$-alkyl" refers to alkyl having 1 to 4 carbon atoms (as defined above), wherein one hydrogen atom of the alkyl radical is replaced by a $C_1$-$C_4$-alkylthio group.

The term "$C_1$-$C_6$-alkylthio" as used herein refers to straight-chain or branched alkyl groups having 1 to 6 carbon atoms (as defined above) bonded via a sulfur atom. Accordingly, the term "$C_1$-$C_6$-haloalkylthio" as used herein refers to straight-chain or branched haloalkyl group having 1 to 6 carbon atoms (as defined above) bonded through a sulfur atom, at any position in the haloalkyl group.

The term "$C_1$-$C_4$-alkoxyimino" refers to a divalent imino radical ($C_1$-$C_4$-alkyl-O—N═) carrying one $C_1$-$C_4$-alkoxy group as substituent, e.g. methylimino, ethylimino, propylimino, 1-methylethyl-imino, butylimino, 1-methylpropylimino, 2-methylpropylimino, 1,1-dimethylethylimino and the like.

The term "$C_1$-$C_6$-alkoxyimino-$C_1$-$C_4$-alkyl" refers to alkyl having 1 to 4 carbon atoms, wherein two hydrogen atoms of one carbon atom of the alkyl radical are replaced by a divalent $C_1$-$C_6$-alkoxyimino radical ($C_1$-$C_6$-alkyl-O—N═) as defined above.

The term "$C_2$-$C_6$-alkenyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkenyloxyimino radical ($C_2$-$C_6$-alkenyl-O—N═).

The term "$C_2$-$C_6$-alkynyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkynyloxyimino radical ($C_2$-$C_6$-alkynyl-O—N═).

The term "hydroxy$C_1$-$C_4$-alkyl" refers to alkyl having 1 to 4 carbon atoms, wherein one hydrogen atom of the alkyl radical is replaced by a OH group.

The term "amino$C_1$-$C_4$-alkyl" refers to alkyl having 1 to 4 carbon atoms, wherein one hydrogen atom of the alkyl radical is replaced by a $NH_2$ group.

The term "$C_1$-$C_6$-alkylamino" refers to an amino group, which is substituted with one residue independently selected from the group that is defined by the term $C_1$-$C_6$-alkyl. Likewise, the term "di$C_1$-$C_6$-alkylamino" refers to an amino group, which is substituted with two residues independently selected from the group that is defined by the term $C_1$-$C_6$-alkyl.

The term "$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a $C_1$-$C_4$-alkyl-NH-group which is bound through the nitrogen. Likewise, the term "di$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a ($C_1$-$C_4$-alkyl)$_2$N— group which is bound through the nitrogen.

The term "aminocarbonyl-$C_1$-$C_4$-alkyl" refers to alkyl having 1 to 4 carbon atoms, wherein one hydrogen atom of the alkyl radical is replaced by a —(C═O)—$NH_2$ group.

The term "$C_2$-$C_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_3$-$C_{11}$-cycloalkyl" refers to a monocyclic, bicyclic or tricyclic saturated univalent hydrocarbon radical having 3 to 11 carbon ring members that is connected through one of the ring carbon atoms by substitution of one hydrogen atom, such as cyclopropyl ($C_3H_5$), cyclobutyl, cyclopentyl, cyclohexyl, cycloheptyl, cyclooctyl, bicyclo[1.1.0]butyl, bicyclo[2.1.0]pentyl, bicyclo[1.1.1]pentyl, bicyclo[3.1.0]hexyl, bicyclo[2.1.1]hexyl, norcaranyl (bicyclo[4.1.0]heptyl) and norbornyl (bicyclo[2.2.1]heptyl). Further examples of bicyclic or tricyclic cycloalkyl radicals are found herein as examples $R^1.1$ to $R^1.57$.

The term "$C_3$-$C_{11}$-cycloalkyl" refers to a monocyclic, bicyclic or tricyclic saturated univalent hydrocarbon radical having 3 to 11 carbon ring members that is connected through one of the ring carbon atoms by substitution of one hydrogen atom, such as cyclopropyl ($C_3H_5$), cyclobutyl, cyclopentyl, cyclohexyl, cycloheptyl, cyclooctyl, bicyclo[1.1.0]butyl, bicyclo[2.1.0]pentyl, bicyclo[1.1.1]pentyl, bicyclo[3.1.0]hexyl, bicyclo[2.1.1]hexyl, norcaranyl (bicyclo[4.1.0]heptyl) and norbornyl (bicyclo[2.2.1]heptyl).

The term "$C_3$-$C_{11}$-cycloalkyl-$C_1$-$C_6$-alkyl" refers to alkyl having 1 to 11 carbon atoms, wherein one hydrogen atom of the alkyl radical is replaced by a $C_3$-$C_{11}$-cycloalkyl group as defined above.

The term "$C_3$-$C_{11}$-cycloalkoxy" refers to a cyclic univalent hydrocarbon radical having 3 to 11 carbon ring members (as defined above) that is bonded via an oxygen, at any position in the cycloalkyl group, for example cyclopropyloxy.

The terms "—C(=O)—$C_1$-$C_4$-alkyl", "—C(=O)—$C_1$-$C_4$-alkoxy" and "—C(=O)—$C_3$-$C_{11}$-cycloalkyl" refer to radicals which are attached through the carbon atom of the —C(=O)— group.

The term "aliphatic" refers to compounds or radicals composed of carbon and hydrogen and which are non-aromatic compounds. An "alicyclic" compound or radical is an organic compound that is both aliphatic and cyclic. They contain one or more all-carbon rings which may be either saturated or unsaturated, but do not have aromatic character.

The terms "cyclic moiety" or "cyclic group" refer to a radical which is an alicyclic ring or an aromatic ring, such as, for example, phenyl or heteroaryl.

The term "and wherein any of the aliphatic or cyclic groups are unsubstituted or substituted with . . . " refers to aliphatic groups, cyclic groups and groups, which contain an aliphatic and a cyclic moiety in one group, such as in, for example, $C_3$-$C_8$-cycloalkyl-$C_1$-$C_4$-alkyl; therefore a group which contains an aliphatic and a cyclic moiety both of these moieties may be substituted or unsubstituted independently of each other.

The term "phenyl" refers to an aromatic ring systems including six carbon atoms (commonly referred to as benzene ring.

The term "heteroaryl" refers to aromatic monocyclic or polycyclic ring systems including besides carbon atoms, 1, 2, 3 or 4 heteroatoms independently selected from the group consisting of N, O and S.

The term "saturated 3- to 7-membered carbocycle" is to be understood as meaning monocyclic saturated carbocycles having 3, 4 or 5 carbon ring members. Examples include cyclopropyl, cyclopentyl, cyclohexyl, cycloheptyl, and the like.

The term "3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms", is to be understood as meaning both, aromatic mono- and bicyclic heteroaromatic ring systems, and also saturated and partially unsaturated heterocycles, for example:

a 3- or 4-membered saturated heterocycle which contains 1 or 2 heteroatoms from the group consisting of N, O and S as ring members such as oxirane, aziridine, thiirane, oxetane, azetidine, thiethane, [1,2]dioxetane, [1,2]dithietane, [1,2]diazetidine;

and a 5- or 6-membered saturated or partially unsaturated heterocycle which contains 1, 2 or 3 heteroatoms from the group consisting of N, O and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydroazepinyl, such as 2,3,4,5-tetrahydro[1H]azepin-1-,-2-,-3-,-4-,-5-,-6- or -7-yl, 3,4,5,6-tetrahydro[2H]azepin-2-,-3-,-4-,-5-,-6- or -7-yl, 2,3,4,7-tetrahydro[1H]azepin-1-,-2-,-3-,-4-,-5-,-6- or -7-yl, 2,3,6,7-tetrahydro[1H]azepin-1-,-2-,-3-,-4-,-5-,-6- or -7-yl, hexahydroazepin-1-,-2-,-3- or -4-yl, tetra- and hexahydrooxepinyl such as 2,3,4,5-tetrahydro[1H]oxepin-2-,-3-,-4-,-5-,-6- or -7-yl, 2,3,4,7-tetrahydro[1H]oxepin-2-,-3-,-4-,-5-,-6- or -7-yl, 2,3,6,7-tetrahydro[1H]oxepin-2-, -3-,-4-,-5-,-6- or -7-yl, hexahydroazepin-1-,-2-,-3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals.

The term "5- or 6-membered heteroaryl" or the term "5- or 6-membered aromatic heterocycle" refer to aromatic ring systems including besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

WORKING EXAMPLES

The present invention is further illustrated by means of the following working examples.

Analytical methods for 3-(p-tolyl)-5-(trifluoromethyl)-1,2,4-oxadiazole: HPLC Agilent 1100 Series; column: Agilent Eclipse-XDB C18, 3.5 um, 4.6×150 mm, Column Flow: 1 mL/min, time: 20 min, solvent: gradient MeCN/H$_2$0 80/20 to 0/100 (0 to 15 min); pressure: 30000 kPa; temperature: 40° C.; wavelength 255 nm; injector volume: 1 uL; retention time of product: 13.6 min (based on reference material).

$^1$H-NMR (δ/ppm, DMSO-d$_6$, 400 MHz): 2.4 (s, 3H), 7.4 (d, 2H), 7.9 (d, 2H).

$^{19}$F-NMR (δ/ppm, DMSO-d$_6$, 400 MHz): 65 (s, 3 F).

Example 1) Preparation of 3-(p-tolyl)-5-(trifluoromethyl)-1,2,4-oxadiazole 5 g (33.3 mmol) solid N'-hydroxy-4-methyl-benzamidine was filled in a pressure reactor equipped with a stirrer. The reactor was heated to 70° C. and purged three times with nitrogen. Then 18 g (300 kPa, 135.8 mmol) trifluoroacetyl chloride was introduced. After the introduction of trifluoroacetyl chloride, the pressure in the reactor was about 400 kPa. The reaction mixture darkened and turned into a liquid very quickly. After 2 hours at 70° C., the HPLC analysis showed >95% conversion, >36 ar % product and <60 ar % by-products.

Example 2) Preparation of 3-(p-tolyl)-5-(trifluoromethyl)-1,2,4-oxadiazole 5 g (33.3 mol) solid N'-hydroxy-4-methyl-benzamidine was filled in a 3-necked round bottom flask equipped with a stirring bar and off-gas scrubber. The flask was heated to 40° C. and 19 g (143.4 mmol) trifluoroacetyl chloride was introduced in 2 hours at atmospheric pressure. Then the temperature was raised to 70° C. and further 11 g (83.0 mmol) trifluoroacetyl chloride was introduced in 2 hours at atmospheric pressure. HPLC analysis showed >99% conversion, >96 ar % product and <3 ar % by-products.

Example 3) Preparation of 3-(p-tolyl)-5-(trifluoromethyl)-1,2,4-oxadiazole 5 g (33.3 mol) solid N'-hydroxy-4-methyl-benzamidine was filled in a 3-necked round bottom flask equipped with a stirring bar, off-gas scrubber and dry ice (solid carbondioxide) cooler. The flask was heated to 65° C. and 12 g (90.6 mmol) trifluoroacetyl chloride were introduced in 90 min at atmospheric pressure. HPLC analysis showed >99% conversion, >96 ar % product and <3 ar % by-products.

Example 4) Preparation of 3-(p-tolyl)-5-(trifluoromethyl)-1,2,4-oxadiazole 15 g (99.3 mol) solid N'-hydroxy-4-methyl-benzamidine was filled in a pressure reactor equipped with a stirrer. The reactor was purged with nitrogen three times and heated to 25° C. Then, 18 g (300 kPa, 135.8 mmol) trifluoroacetyl chloride was introduced. After the introduction of trifluoroacetyl chloride, the pressure in the reactor was about 400 kPa. After 2 hours, the pressure was released and a sample was taken for HPLC analysis, showing about 5 ar % of the product. Then, another 19 g (300 kPa, 143.4 mmol) trifluoroacetylchloride was introduced and the reactor was heated to 60° C. for 2 hours, showing 23 ar % product. Heating to 70° C., and introducing 20 g (300 kPa, 150.9 mmol) trifluoroacetyl chloride yielded full conversion after 4 hours and 25.5 g of a clear slightly yellow liquid. HPLC analysis showed >99% conversion, >97 ar % product and <2 ar % by-products.

Example 5) Preparation of 3-(p-tolyl)-5-(trifluoromethyl)-1,2,4-oxadiazole 15 g (99.3 mmol) solid N'-hydroxy-4-methyl-benzamidine was filled in a pressure reactor equipped with a stirrer. The reactor was heated to 50° C. and purged with nitrogen three times. Then 100 kPa of nitrogen, followed by 19 g (350 kPa, 143.4 mmol) trifluoroacetyl chloride were introduced within 30 minutes. After the introduction of trifluoroacetyl chloride, the pressure in the reactor was about 550 kPa. After 2 hours, the temperature was raised to 80° C. for 1 hour. The pressure was released to 100 kPa and another 8 g (300 kPa, 60.4 mmmol) trifluoroacetyl chloride were introduced, after 2 additional hours and repeated pressure release, 81 ar % product was observed. Heating to 70° C., and introducing 5 g (150 kPa, 37.7 mmol) trifluoroacetyl chloride yielded full conversion after 2 hours. The pressure was released and 27 g of a clear slightly yellow liquid was obtained. HPLC analysis showed >99% conversion, >96 ar % product and <4 ar % by-products. Quantitative NMR measurement showed 76.6% product and 23.8% TFA, corresponding to 92% yield.

Example 6) Preparation of 3-(p-tolyl)-5-(trifluoromethyl)-1,2,4-oxadiazole 15 g (99.3 mmol) solid N'-hydroxy-4-methyl-benzamidine was filled in a pressure reactor equipped with a stirrer. The reactor was heated to 70° and purged with nitrogen three times. Then 100 kPa of nitrogen, followed by 14.5 g (350 kPa, 109.4 mmol) trifluoroacetyl chloride were introduced within 5 minutes. After the introduction of trifluoroacetyl chloride, the pressure in the reactor was about 550 kPa. After 2 hours, the pressure was decreased to 100 kPa and another 11.5 g (200 kPa, 86.8 mmol) trifluoroacetyl chloride were introduced, showing 85 ar % product after 2 hours. Heating to 70° C., and introducing 5 g (100 kPa, 37.7 mmol) trifluoroacetyl chloride yielded full conversion after 2 hours. The pressure was released and 21.5 g of a clear slightly yellow liquid was obtained. HPLC analysis showed >99% conversion, >92 ar % product and <7 ar % by-products.

Example 7) Preparation of 3-[4-(trichloromethyl)phenyl]-5-(trifluoromethyl)-1,2,4-oxadiazole 300 g (1.31 mol) 3-(p-tolyl)-5-(trifluoromethyl)-1,2,4-oxadiazole was placed in a 500 mL quartz glass round bottom flask. 427 g chlorine (6.0 mol) was passed into the reactor, heated to 125° C., and irradiated with a Heraeus TQ 150 Watt (mercury medium pressure emitter) UV-lamp over 8 hours. After completion of the reaction the reaction mass was stripped with nitrogen to remove remaining chlorine and hydrogen chloride gas. GC analysis showed 98.7 ar % product. Yield: 437 g crystalline product; 99%; melting point: 75° C.-78° C.; $^1$H-NMR (CDCl$_3$): 8.1 ppm (m, 2H, 2×CH); 8.3 ppm (m, 2H, 2×CH).

Example 8) Preparation of N-(2-fluorophenyl)-4-[5-(trifluoromethyl)-1,2,4-oxadiazol-3-yl]benzamide 150 g (0.446 mol) solid 3-[4-(trichloromethyl)phenyl]-5-(trifluoromethyl)-1,2,4-oxadiazole and 3.75 g (0.023 mol) iron(III)-chloride was filled in a 0.75 L reactor equipped with an overhead stirrer, reflux condenser and off-gas scrubber. The reactor was heated to 120° C. and 7.6 g (0.422 mol) water was dosed into the reaction mixture within 3 hours and stirred for another 30 minutes. Then the reaction mixture was cooled to 25° C. and 300 g (4.156 mol) tetrahydrofuran was added and the reaction mixture cooled to 10° C. Then a solution of 56 g 2-fluoro-aniline (0.489 mol), 50 g triethylamine (0.489 mol) and 200 g tetrahydrofuran (2.771 mol) was added in about 40 minutes, whereas the temperature of the reaction mixture was kept between 10° C. and 25° C. and the lines were flushed with 100 g (1.4 mol) tetrahydrofuran. After stirring overnight, the mixture was cooled to 5° C. and 450 mL water was added. The solid was filtered off and washed twice with 100 g cold water. A solid material was obtained, which was dried (80° C., 2 kPa) to yield 130 g (0.363 mol) of the title product. HPLC analysis showed >98 ar % product.

Example 9) Preparation of N-methyl-4-[5-(trifluoromethyl)-1,2,4-oxadiazol-3-yl]benzamide 5 g (0.015 mol) solid 3-[4-(trichloromethyl)phenyl]-5-(trifluoromethyl)-1,2,4-oxadiazole and 0.12 g (0.74 mmol) iron(III)-chloride was filled in a 0.75 L reactor equipped with an overhead stirrer, reflux condenser and off-gas scrubber. The reactor was heated to 85° C. and 0.26 g (0.014 mol) water were dosed into the reaction mixture within 1 hour and stirred for another 40 minutes. Then the temperature was cooled to 25° C. and 14.6 g (0.222 mol) tetrahydrofuran was added and the reaction mixture cooled to 0° C. Then 27 mL (5M, 0.074 mmol) of a methylamine solution in tetrahydrofuran was added and stirred overnight at room temperature. Water and ethyl acetate were added and the phases separated. The organic phase was washed with water and dried over magnesium sulfate/activated carbon. Filtration and removal of the volatiles yielded 2.9 g (88 ar %, 0.091 mol, retention time=0.93 min, M+=271) N-methyl-4-[5-(trifluoromethyl)-1,2,4-oxadiazol-3-yl]benzamide.

Example 10) Preparation of N-methyl-4-[5-(trifluoromethyl)-1,2,4-oxadiazol-3-yl]benzenecarbothioamide 15 g (54.8 mmol) N-methyl-4-[5-(trifluoromethyl)-1,2,4-oxadiazol-3-yl]benzamide and 3.8 g (16.9 mmmol) phosphorus(V) sulfide was dissolved in 87 g toluene and heated to 112° C. for 1 hour. The reaction mixture was treated below 100° C. with 100 g water and 100 g toluene. After phase separation at 75° C. the organic phase was separated and washed with 100 g water. The volatiles were removed in vacuo (80° C., 200 to 5 mbar) to yield 15.8 g of crude product, which was suspended in 50 mL diisopropylether and heated to 60° C. for 1 hour. After cooling to room temperature, the precipitate was filtered off and washed with 20 mL diisopropylether. After drying at 80° C. and at reduced pressure, 13.5 g (44.2 mmol, 94 ar %) N-methyl-4-[5-(trifluoromethyl)-1,2,4-oxadiazol-3-yl]benzenecarbothioamide was obtained. $^1$H-NMR (δ/ppm, CDCl$_3$, 400 MHz): 3.4 ppm, s, 3H; 7.8, s, br 1H; 7.9, d, 2H; 8.1, d, 2H)

The invention claimed is:
1. A process for preparing compounds of formula I,

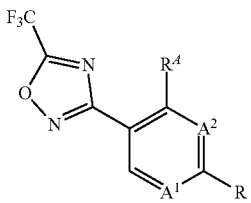

wherein
$A^1$ is N or CH;
$A^2$ is N or CH;
$R^A$ is hydrogen or halogen;
R is methyl, trichloromethyl, ethyl, iso-propyl, OH, SH, cyano, halogen, CH$_2$F, CHF$_2$, 2,2,2-trifluoroethyl, cyclopropyl, —COOH, —COOR$^1$, —C(=W)NR$^1$R$^2$, —CR$^3$R$^4$NR$^1$R$^2$, —CR$^3$R$^4$OR$^1$, —CR$^3$(=NR$^1$), —CR$^3$(=O), —CR$^3$R$^4$COOH, —CR$^3$R$^4$COR$^1$—CR$^3$R$^4$C(=W)NR$^1$R$^2$, —OCR$^3$R$^4$COOH, —OCR$^3$R$^4$COR$^1$, —OCR$^3$R$^4$C(=W)NR$^1$R$^2$, —CR$^3$R$^4$NR$^2$C(=W)R$^1$, —CR$^3$R$^4$S(=O)$_2$R$^1$, or —CR$^3$R$^4$NR$^2$S(=O)$_2$R$^1$;
W is O or S;
$R^2$ is selected from the group consisting of hydrogen, formyl, C$_1$-C$_6$-alkyl, C$_2$-C$_6$-alkenyl, C$_2$-C$_6$-alkynyl, C$_1$-C$_6$-alkoxy, C$_3$-C$_{11}$-cycloalkyl, C$_3$-C$_6$-cycloalkenyl, C$_3$-C$_{11}$-cycloalkyl-C$_1$-C$_4$-alkyl, phenyl-C$_1$-C$_4$-alkyl, phenyl, pyridinyl, —C(=O)—(C$_1$-C$_6$-alkyl), —C(=O)—(C$_3$-C$_{11}$-cycloalkyl), —C(=O)—(C$_1$-C$_6$-alkoxy) and —N(R$^{2a}$)$_2$;
$R^{2a}$ is independently selected from the group consisting of hydrogen, OH, C$_1$-C$_6$-alkyl, C$_2$-C$_6$-alkenyl, C$_2$-C$_6$-alkynyl, C$_3$-C$_{11}$-cycloalkyl, C$_3$-C$_8$-cycloalkenyl, C$_1$-C$_6$-alkoxy, C$_1$-C$_4$-alkoxy-C$_1$-C$_4$-alkyl and C$_1$-C$_6$-alkylthio;
and wherein any of the aliphatic or cyclic groups in $R^2$ are unsubstituted or substituted with 1, 2, 3 or up to the maximum possible number of identical or different radicals selected from the group consisting of halogen, hydroxy, oxo, cyano, C$_1$-C$_6$-alkyl, C$_1$-C$_6$-alkoxy and C$_3$-C$_{11}$-cycloalkyl;
$R^1$ is C$_1$-C$_6$-alkyl, C$_1$-C$_6$-alkoxy, C$_3$-C$_{11}$-cycloalkyl, C$_3$-C$_8$-cycloalkenyl, C$_2$-C$_6$-alkenyl, C$_2$-C$_6$-alkynyl, C$_1$-C$_6$-alkoxyimino-C$_1$-C$_4$-alkyl, C$_2$-C$_6$-alkenyloxyimino-C$_1$-C$_4$-alkyl, C$_2$-C$_6$-alkynyloxyimino-C$_1$-C$_4$-alkyl, C$_1$-C$_6$-alkylamino, diC$_1$-C$_6$-alkylamino, —C(=O)—(C$_1$-C$_6$-alkyl), —C(=O)—(C$_1$-C$_6$-alkoxy), phenyl-C$_1$-C$_4$-alkyl, phenyl-C$_1$-C$_4$-alkenyl, phenyl-C$_1$-C$_4$-alkynyl, heteroaryl-C$_1$-C$_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from the group consisting of N, O and S as ring member atoms with the provision that the heterocycle cannot contain 2 contiguous atoms selected from O and S; and wherein the heteroaryl group in the group heteroaryl-C$_1$-C$_4$-alkyl is a 5- or 6-membered aromatic heterocycle, wherein the ring member atoms of the heterocyclic ring include besides carbon atoms 1, 2, 3 or 4 heteroatoms selected from the group consisting of N, O and S as ring member atoms with the provision that the heterocycle cannot contain 2 contiguous atoms selected from the group consisting of 0 and S; and wherein any of the abovementioned aliphatic or cyclic groups are unsubstituted or substituted with 1, 2, 3 or up to the maximum possible number of identical or different groups R$^{1a}$; or
$R^1$ and $R^2$, together with the nitrogen atom to which $R^2$ is attached, and together with interjacent group —C(=W)—, if present, which is located between said nitrogen atom and the group R$^1$, form a saturated or partially unsaturated mono- or bicyclic 3- to 10-membered heterocycle, wherein the heterocycle includes beside one nitrogen atom and one or more carbon atoms no further heteroatoms or 1, 2 or 3 further heteroatoms independently selected from the group consisting of N, O and S as ring member atoms with the provision that the heterocycle cannot contain 2 contiguous atoms selected from the group consisting of 0 and S; and wherein the heterocycle is unsubstituted or substituted with 1, 2, 3, 4 or up to the maximum possible number of identical or different groups $R^{1a}$; or if $R^2$ is —N($R^{2a}$)$_2$, $R^1$ and one of the two groups $R^{2a}$, together with the nitrogen atom to which $R^{2a}$ is attached, and together with interjacent groups, which are located between said nitrogen atom and the group $R^1$, form a saturated or partially unsaturated mono- or bicyclic 3- to 10-membered heterocycle, wherein the heterocycle includes beside two nitrogen atoms and one or more carbon atoms no further heteroatoms or 1, 2 or 3 further heteroatoms independently selected from the group consisting of N, O and S as ring member atoms with the provision that the heterocycle cannot contain 2 contiguous atoms selected from the group consisting of O and S; and wherein the heterocycle is unsubstituted or substituted with 1, 2, 3, 4 or up to the maximum possible number of identical or different groups $R^{1a}$;

$R^{1a}$ is halogen, oxo, cyano, $NO_2$, OH, SH, $NH_2$, $C_1$-$C_6$-alkyl, $C_1$-$C_6$-haloalkyl, $C_1$-$C_8$-alkoxy, $C_1$-$C_6$-haloalkoxy, $C_1$-$C_6$-alkylthio, $C_1$-$C_6$-haloalkylthio, $C_3$-$C_8$-cycloalkyl, —NHSO$_2$-$C_1$-$C_4$-alkyl, (C=O)—$C_1$-$C_4$-alkyl, C(=O)—$C_1$-$C_4$-alkoxy, $C_1$-$C_6$-alkylsulfonyl, hydroxy$C_1$-$C_4$-alkyl, C(=O)—$NH_2$, C(=O)—NH($C_1$-$C_4$-alkyl), $C_1$-$C_4$-alkylthio-$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl or $C_1$-$C_4$-alkoxy-$C_1$-$C_4$-alkyl;

$R^3$, $R^4$ independently of each other are selected from the group consisting of hydrogen, halogen, cyano, $C_1$-$C_4$-alkyl, $C_1$-$C_4$-alkenyl, $C_1$-$C_4$-alkynyl, $C_1$-$C_4$-haloalkyl and $C_1$-$C_4$-alkoxy; or $R^3$ and $R^4$ together with the carbon atom to which they are bound form a cyclopropyl group;

the process comprising reacting a compound of formula II,

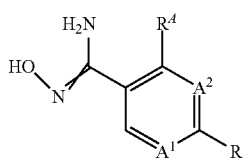

II wherein the variables $A^1$, $A^2$, R and $R^4$ are as defined above for compounds of formula I, with a trifloroacetyl halide of formula IIa,

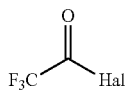

IIa wherein Hal is chlorine or fluorine; and whereas the process is characterized in that the compounds of formula II and IIa are used in substance.

2. The process of claim 1, wherein Hal in compound IIa is chlorine.

3. The process of claim 1, wherein R in compounds I and II is methyl, trichloromethyl, COOH, OH, SH, cyano or halogen.

4. The process of claim 1, wherein $A^1$ and $A^2$ are CH and $R^4$ is hydrogen or fluorine in compounds I and II.

5. The process of claim 1, wherein the process is conducted at a temperature between −40° C. and 100° C.

6. The process of claim 1, wherein the process is conducted at a temperature between 0° C. and 100° C.

7. The process of claim 1, wherein the process is conducted at a pressure between 100 and 1000 kPa.

8. The process of claim 1, wherein R in compounds I and II is methyl, and further comprising the step of reacting the compound of formula I to obtain a compound of formula Ib

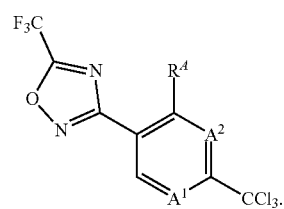

Ib

9. The process of claim 8, further comprising the step of reacting the compound of formula Ib to obtain a compound of formula III

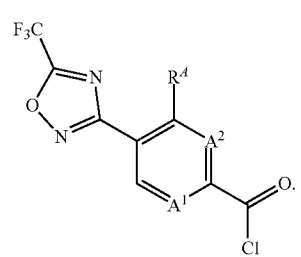

III

10. The process of claim 9, wherein the step of reacting the compound of formula Ib to obtain a compound of formula III is carried out in the presence of iron(III) chloride and water.

11. The process of claim 9, further comprising the step of reacting the compound of formula III with a compound of formula IV

$R^1$—NH—$R^2$     IV, wherein $R^1$ and $R^2$ in the compound of formula IV is as defined in claim 1 to obtain a compound of formula Ic

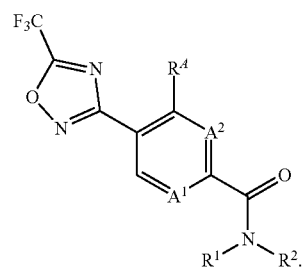

Ic

12. The process of claim 11, further comprising the step of reacting the compound of formula Ic to obtain a compound of formula Id

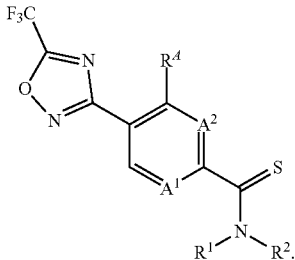

Id

13. The process of claim 11, wherein
$A^1$ and $A^2$ are CH;
$R^a$ is hydrogen or fluorine;
$R^1$ is selected from the group consisting of $C_1$-$C_6$-alkyl, $C_2$-$C_6$-alkenyl, $C_2$-$C_6$-alkynyl, $C_1$-$C_6$-alkoxyimino-$C_1$-$C_4$-alkyl, $C_3$-$C_{11}$-cycloalkyl, $C_3$-$C_8$-cycloalkenyl, phenyl-$C_1$-$C_4$-alkyl, heteroaryl-$C_1$-$C_4$-alkyl, phenyl or heteroaryl; and wherein the heteroaryl group is a 5- or 6-membered aromatic heterocycle, wherein the ring includes besides carbon atoms 1, 2, 3 or 4 heteroatoms selected from the group consisting of N, O and S as ring member atoms; and wherein any of the aliphatic or cyclic groups are unsubstituted or substituted with 1, 2, 3 or up to the maximum possible number of identical or different radicals selected from the group consisting of halogen, cyano, $C_1$-$C_6$-alkyl and $C_1$-$C_6$-alkoxy;
$R^2$ is selected from the group consisting of hydrogen, formyl, $C_1$-$C_6$-alkyl, $C_1$-$C_6$-alkoxy, $C_2$-$C_6$-alkenyl, propargyl, $C_3$-$C_8$-cycloalkyl, $C_3$-$C_8$-cycloalkenyl, $C_3$-$C_8$-cycloalkyl-$C_1$-$C_4$-alkyl, phenyl, $C_1$-$C_6$-alkylamino or di$C_1$-$C_6$-alkylamino; and wherein any of the aliphatic or cyclic groups are unsubstituted or substituted with 1, 2, 3, 4 or up to the maximum possible number of identical or different radicals selected from the group consisting of halogen, cyano, $C_1$-$C_6$-alkyl and $C_1$-$C_6$-alkoxy.

14. The process of claim 12, wherein
$A^1$ and $A^2$ are CH;
$R^a$ is hydrogen or fluorine;
$R^1$ is methyl, ethyl, n-propyl, iso-propyl, n-butyl, sec-butyl, iso-butyl, cyclopropyl, 2-methoxyiminoethyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, methyl, ethyl, methoxy, trifluoromethyl, trifluoromethoxy, difluoromethyl, difluoromethoxy and cyclopropyl;
$R^2$ is hydrogen, methyl or ethyl.

15. The process of claim 12, wherein
$A^1$ and $A^2$ are CH;
$R^a$ is hydrogen or fluorine;
$R^1$ is methyl, 2-methoxyiminoethyl, bicyclo[1.1.1]pentan-1-yl, 2-fluoro-phenyl, 4-fluoro-phenyl or 2-difluoromethoxy-phenyl;
$R^2$ is hydrogen.

16. The process of claim 2, wherein R in compounds I and II is methyl, trichloromethyl, COOH, OH, SH, cyano or halogen.

17. The process of claim 2, wherein $A^1$ and $A^2$ are CH and $R^A$ is hydrogen or fluorine in compounds I and II.

18. The process of claim 2, wherein the process is conducted at a temperature between −40° C. and 100° C.

19. The process of claim 2, wherein the process is conducted at a temperature between 0° C. and 100° C.

20. The process of claim 2, wherein the process is conducted at a pressure between 100 and 1000 kPa.

* * * * *